United States Patent [19]

Shimada et al.

[11] Patent Number: 5,833,882
[45] Date of Patent: Nov. 10, 1998

[54] DETECTING AGENT

[75] Inventors: Takashi Shimada; Youji Nawa, both of Kanagawa-ken, Japan

[73] Assignee: Japan Pionics Co., Ltd., Tokyo, Japan

[21] Appl. No.: 866,961

[22] Filed: Jun. 2, 1997

[30] Foreign Application Priority Data

Aug. 23, 1996 [JP] Japan .................................. 8-241349

[51] Int. Cl.$^6$ .......................... G01N 21/77; G01N 21/80; G08B 17/117
[52] U.S. Cl. .......................... 252/408.1; 422/56; 422/86; 422/88; 436/84; 436/183; 502/241; 502/259; 502/260; 502/405; 502/439
[58] Field of Search ............................. 48/193; 422/55, 422/86, 88; 252/408.1, 56, 181.6; 502/259, 439, 260, 241, 405; 436/84, 183

[56] References Cited

U.S. PATENT DOCUMENTS

| | | | |
|---|---|---|---|
| 3,350,175 | 10/1967 | McConnaughey et al. | 23/254 |
| 3,691,380 | 9/1972 | Hubner et al. | 250/83 |
| 3,743,846 | 7/1973 | Matsumoto et al. | 250/474 |
| 3,899,677 | 8/1975 | Hori et al. | 250/474 |
| 3,904,373 | 9/1975 | Harper | 23/253 TP |
| 4,023,930 | 5/1977 | Blunck et al. | 23/232 R |
| 4,731,333 | 3/1988 | Kitahara et al. | 436/72 |
| 4,795,611 | 1/1989 | van der Smissen | 422/56 |
| 5,030,610 | 7/1991 | Sakata et al. | 502/400 |
| 5,171,536 | 12/1992 | Evers | 422/88 |
| 5,267,532 | 12/1993 | Franklin et al. | 119/173 |
| 5,665,313 | 9/1997 | Shimada et al. | 422/86 |

FOREIGN PATENT DOCUMENTS

| | | |
|---|---|---|
| 0 585 212 A2 | 3/1994 | European Pat. Off. . |
| 36 14 723 C1 | 10/1987 | Germany . |
| 38 26 090 A1 | 2/1990 | Germany . |
| 1057984 | 2/1967 | United Kingdom . |

OTHER PUBLICATIONS

Database WPI, Section Ch, Week 7939, Derwent Publications Ltd., London GB; Class D15, AN 79–70679B of JP 54 104 638 A (Mitsubishi Heavy Ind. Co. Ltd.), 17 Aug. 1979.

*Primary Examiner*—Joseph K. McKane
*Assistant Examiner*—Deanna Baxam
*Attorney, Agent, or Firm*—Frishauf, Holtz, Goodman, Langer & Chick, P.C.

[57] ABSTRACT

A detecting agent for detecting at least one member selected from the group consisting of halogen gases and acidic gases which is contained in a gas, wherein the detecting agent comprises a discoloring component which comprises a hydroxide of a transition metal and Congo Red. Halogen gases and acidic gases which are contained in hydrogen, nitrogen, argon, or helium can be detected under a dry condition with a high sensitivity in accordance with the present invention.

16 Claims, No Drawings

DETECTING AGENT

BACKGROUND OF THE INVENTION

1. Field of the Invention

The present invention relates to a detecting agent for detecting a halogen gas and/or an acidic gas. More particularly, the present invention relates to a detecting agent for detecting a halogen gas and/or an acidic gas contained in a gas, such as nitrogen, hydrogen, argon, and helium.

2. Description of the Related Arts

With the growth of the semiconductor industries and the optoelectronics industries, various types of halogen gas and acidic gas are recently introduced into these industries, and the amounts of the above gases used in these industries are increasing.

In the silicon semiconductor manufacturing process or compound semiconductor manufacturing process, the halogen gases and the acidic gases are all indispensable for growing or etching films of crystalline silicon, amorphous silicon, or silicon oxide.

However, all of these gases are highly toxic. The threshold limit values in time weighted average (TLV-TWA) of chlorine and fluorine which are particularly toxic are each 1 ppm. Therefore, the concentrations of these gases in the working environment must always be measured during handling of these gases. When leakage of these gases occurs, it is required that the leaked gas be detected without fail, and appropriate safety measures be taken.

Moreover, a waste gas discharged from a semiconductor manufacturing process contains these gases. Therefore, when the waste gas is discharged to the atmosphere after the waste gas is purified by using an exhaust gas treatment equipment, it is required that the complete removal of the halogen gases and the acidic gases be confirmed.

The methods heretofore known for detecting a halogen gas include (i) ortho-tolidine method and (ii) a method in which the bleaching activity of a halogen gas is utilized. The methods heretofore known for detecting an acidic gas include (iii) a method in which a pH indicator is used as the discoloring component and (iv) a method in which a hydrogen halide is formed from the acidic gas and water, and the change in pH by the formed the hydrogen halide is used for the detection.

Many types of detecting tube and detector which are prepared by packing a detecting agent, such as those described above, into a glass tube or a vessel, are brought into contact with the gases to be examined, and detect the above gases by discoloration when the above gases are present have been known.

However, (i) the ortho-tolidine method, (ii) the method in which the discoloring activity of a halogen gas is utilized, and (iv) the method in which a hydrogen halide is formed from the acidic gas and water and the change in pH by the formed the hydrogen halide is used for the detection are all conducted in a wet condition or require a reaction condition of a high humidity. These methods cannot practically be used in a dry condition because moisturizing is necessary for detection of halogen gases or acidic gases in a gas to be examined and also because the response of the detection is slow.

Although (iii) the method in which a pH indicator is used as the discoloring component can be conducted in a dry condition, drawbacks are found in that all pH indicators show the discoloration only to a small degree and achieving the detection with a high sensitivity is difficult, and that the sensitivity is still more decreased when the detecting component in the detector is dried.

SUMMARY OF THE INVENTION

Under the above circumstances, development of a detecting agent which can detect a halogen gas and an acidic gas with a high sensitivity even in a dry condition and can maintain the detecting ability for a long time with stability has strongly been desired.

As the result of the present inventors to solve the above problems and to obtain a detecting agent which shows rapid discoloration with a high sensitivity even when the detecting agent is brought into contact with a dilute halogen gas or acidic gas, it was discovered that an excellent detecting agent can be obtained by using a combination of a hydroxide of a transition metal and Congo Red as the discoloring component. The present invention has been completed on the basis of the discovery.

Thus, the present invention provides a detecting agent for detecting at least one member selected from the group consisting of halogen gases and acidic gases which is contained in a gas, wherein the detecting agent comprises a discoloring component which comprises a hydroxide of a transition metal and Congo Red.

DESCRIPTION OF THE PREFERRED EMBODIMENTS

The detecting agent of the present invention can be applied to detection of a halogen gas and/or an acidic gas contained in nitrogen, hydrogen, argon, or helium.

The halogen gas which is detected by the detecting agent of the present invention is a gas composed of halogen atoms alone. Examples of the halogen gas include gases of fluorine, chlorine, bromine, chlorine fluoride, and chlorine trifluoride. The acidic gas includes a gas which is acidic by itself and a gas which exhibits the acidity when the gas is brought into contact with water and hydrolyzed. Examples of the acidic gas include hydrogen fluoride, tungsten hexafluoride, silicon tetrafluoride, boron trifluoride, hydrogen chloride, silicon tetrachloride, and boron trichloride.

The detecting agent of the present invention comprises a discoloring component which comprises a hydroxide of a transition metal and Congo Red. The color of the discoloring component sensitively changes from the original color of persimmon to red into a different color of black when the discoloring component is brought into contact with a halogen gas and from the original color of persimmon to red color into a different color of blue to dark blue when the discoloring component is brought into contact with an acidic gas.

In the present invention, a hydroxide of a transition metal is used as a component of the discoloring component of the detecting agent. Examples of the transition metal include nickel (II), cobalt (II), manganese (II), and combinations of these metals. As the hydroxide of the transition metal, nickel hydroxide $(Ni(OH)_2)$, cobalt hydroxide $(Co(OH)_2)$, and manganese hydroxide $(Mn(OH)_2)$ can be used singly or in combination.

Nickel (II) hydroxide is a light green crystal and can be prepared by adding an aqueous solution of potassium hydroxide or sodium hydroxide into an aqueous solution of nickel (II) nitrate or nickel (II) sulfate. A commercial nickel (II) hydroxide may also be used. Nickel (II) hydroxide containing a small amount of nickel (I) hydroxide or nickel (III) hydroxide may be used for the detecting agent of the present invention as along as the color tone of nickel (II) hydroxide is not adversely affect to a great extent.

Cobalt (II) hydroxide is a light blue or rose crystal and can be prepared by adding an aqueous solution of potassium hydroxide or sodium hydroxide into an aqueous solution of cobalt (II) nitrate. Because the color of cobalt (II) hydroxide relatively easily changes into green by oxidation, cobalt (II) hydroxide is preferably handled under an inert gas.

Manganese (II) hydroxide is a white crystal and can be prepared by adding an aqueous solution of potassium hydroxide or sodium hydroxide into an aqueous solution of manganese (II) nitrate. Because the color of manganese (II) hydroxide relatively easily changes into brown by oxidation, manganese (II) hydroxide is preferably handled under an inert gas.

Congo Red which is the other component of the discoloring component in the present invention is widely used as an ordinary pH indicator. A commercial product can be used.

In the present invention, the discoloring component comprising a mixture of a hydroxide of a transition metal and Congo Red may be used for the detecting agent in the form of powder, after forming into pellets, or in the form supported on an inorganic support.

When the mixture of a hydroxide of a transition metal and Congo Red is used for the detecting agent in the form of powder or after being formed into pellets, the ratio by weight of the hydroxide of a transition metal to Congo Red is in the range of 1:(0.01 to 0.00001), preferably in the range of 1:(0.005 to 0.0001). When the amount of Congo Red is less than the above range, the effect of Congo Red is not clearly exhibited. When the amount of Congo Red is more than the above range, the discoloration is not clearly exhibited when some type of hydroxide of a transition metal is used. The mixture can be used after being formed into pellets or granules in accordance with a conventional dry or wet forming process. In the process of forming the mixture into pellets or granules, a small amount of lubricating agent or a forming agent which is inert to the hydroxide of a transition metal and Congo Red may be used in order to facilitate the forming, where necessary.

In the present invention, the discoloring component comprising the mixture of a hydroxide of a transition metal and Congo Red can be used in the form supported on a support. It is particularly preferred that cobalt hydroxide is used in the form supported on a support because cobalt hydroxide cannot easily be handled with stability.

The inorganic support on which the mixture of a hydroxide of a transition metal and Congo Red is supported can suitably be selected from conventional inorganic supports. A support for a catalyst, such as silica gel, silica-alumina, alumina, zirconia, and titania, may be used singly or in combination. Among these supports, white or colorless supports are preferable, and silica gel is particularly preferable. Commercial silica gel which is generally available as a drying agent has a specific surface area of about 450 to 800 $cm^2/g$ and may be used as the inorganic support. However, it is preferred for more fully achieving the object of the present invention that silica-gel having a specific surface area of 50 to 400 $cm^2/g$ which is prepared by the hydrothermal synthesis is used. When the specific surface area is less than this range, the rate of discoloration is occasionally decreased.

For preparing the supported discoloring component, the support can be dipped into a fluid prepared by dissolving or suspending the discoloring component in water or in an organic solvent, or a solution or a suspension of the discoloring component can be sprayed on the surface of the support while the support is stirred.

The ratio by weight of the support to the hydroxide of a transition metal and Congo Red (the inorganic support:the hydroxide of a transition metal:Congo Red, by weight) is generally in the range of 1:(0.15 to 0.0001):(0.1 to 0.00001), preferably 1:(0.05 to 0.005):(0.01 to 0.0001). When the amount of the hydroxide of a transition metal relative to the amount of the inorganic support is less than the above range, the sufficient sensitivity is occasionally not obtained. When the amount of the hydroxide of a transition metal is more than the above range, the change in color is occasionally not clearly exhibited. When the amount of Congo Red relative to the amount of the inorganic support is less than the above range, the sufficient sensitivity is occasionally not obtained. When the amount of the hydroxide of Congo Red is more than the above range, the change in color is occasionally not clearly exhibited.

In order to prevent oxidation of the hydroxide of a transition metal during the preparation of the detecting agent, it is preferred in the present invention that the procedures for supporting the discoloring component and drying the supported detecting agent are conducted under an atmosphere of nitrogen. It is also preferred that the obtained detecting agent is stored in such a condition that the detecting agent makes no contact with oxygen.

The speed of the gas to be examined which is brought into contact with the detecting agent is not particularly limited. In a semiconductor equipment or an exhaust gas treatment equipment, the superficial veocity in a column is generally about 0.01 to 100 cm/sec. When the equipment is purged, the superficial velocity in a column is sometimes more than 100 cm/sec. In general, when the velocity is lower than the above range, the discoloration is occasionally slower, and when the velocity is higher than the above range, there is the possibility that the pressure loss is increased.

When the gas to be examined is brought into contact with the detecting agent, the temperature of the gas to be examined is generally $-20°$ to $100°$ C., and the pressure of the gas to be examined is generally about 0.001 to 20 $kg/cm^2$ abs.

The detecting agent of the present invention is solid and generally packed into a detecting tube made of glass, a transparent container, such as a transparent container made of a transparent plastic, or the part of a viewing window disposed in a cleaning cylinder for a gas. The presence of a halogen or an acidic gas contained in the gas to be examined can be found by discoloration of the detecting agent. When the detecting agent of the present invention is used in combination with a cleaning agent, the detecting agent can be used by packing the detecting agent into the cleaning cylinder at a position which is at the downstream of the layer of the cleaning agent or between a plurality of layers of the cleaning agent or by connecting a detecting cylinder packed with the detecting agent after the cleaning cylinder.

When the detecting agent is used in the manner described above, the color of the detecting agent sensitively changes from the original color of persimmon to red into a different color of black when the detecting agent is brought into contact with a halogen gas and from the original color of persimmon to red color into a different color of blue to dark blue when the detecting agent is brought into contact with an acidic gas, and thus these gases in the gas to be examined can easily be detected.

Accordingly, the detecting agent of the present invention has the following advantageous properties:

(i) Because moisture is not required for detecting a halogen gas and an acidic gas, the halogen gas and the acidic gas can always be detected with a high sensitivity independently of the moisture content in the gas to be examined and the detecting agent.

(ii) Because the color of the detecting agent changes from a bright color to a dark color when the detecting agent is brought into contact with a halogen gas or an acidic gas, the difference in color before and after the change in color is large, and the easy and sensitive detection is enabled.

The present invention is described more specifically with reference to examples in the following. However, the present invention is not limited by the examples.

EXAMPLE 1 TO 9

(Preparation of a detecting agent 1)

Granular silica gel having a grain size of 5 to 10 mesh, a specific surface area of 325 $m^2/g$, a pore volume of 0.99 ml/g, and a bulk density of 0.420 g/ml (a product of FUJI SILICIA KAGAKU Co., Ltd.; CARRYACT-10) in an amount of 100 g was impregnated with a solution prepared by dissolving 5.0 g of cobalt nitrate hexahydrate into 153 ml of water. After 50 ml of a 1N aqueous solution of sodium hydroxide was added to the impregnated product and the components were mixed together, the obtained mixture was dried in vacuo by using a rotary evaporator at a temperature of 50° C. To the obtained product, a solution prepared by dissolving 0.1 g of Congo Red into 100 ml of water was added, and the components were mixed together. The resultant mixture was completely dried again in vacuo by using a rotary evaporator to prepare a detecting agent.

(Measurement of the detecting ability 1)

Nine glass tubes having an inner diameter of 19 mm were packed each with 2.0 g of the detecting agent prepared above. Nitrogen gas containing 10 ppm or 1 ppm of chlorine, 50 ppm or 5 ppm of hydrogen chloride, 10 ppm of bromine, 10 ppm of fluorine, 50 ppm of boron trifluoride, 50 ppm of tungsten hexafluoride, or 10 ppm of chlorine trifluoride was passed through the glass tubes packed with the detecting agent at the superficial velocity in a column of 5.9 cm/sec to bring the detecting agent into contact with the gas, and the time passed before the discoloration started was measured.

The results are shown in Table 1.

TABLE 1

| | gas to be detected | | time before start |
|---|---|---|---|
| | type | concentration (ppm) | of discoloration (min) |
| Example 1 | chlorine | 10 | <1 |
| Example 2 | chlorine | 1 | 35 |
| Example 3 | hydrogen chloride | 50 | <1 |
| Example 4 | hydrogen chloride | 5 | 28 |
| Example 5 | bromine | 10 | <0.5 |
| Example 6 | fluorine | 10 | <1 |
| Example 7 | boron trichloride | 50 | <1 |
| Example 8 | tungsten hexafluoride | 50 | <1 |
| Example 9 | chlorine trifluoride | 10 | <1 |

EXAMPLES 10 AND 11

(Preparation of a detecting agent 2)

The same granular silica gel as that used in Example 1 in an amount of 100 g was impregnated with a solution prepared by dissolving 20.0 g of nickel nitrate hexahydrate into 153 ml of water. After 250 ml of a 1N aqueous solution of sodium hydroxide was added to the impregnated product, the components were mixed together. The resultant mixture was left standing with intermittent stirring for 12 hours to allow the reaction to proceed. The supernatant fluid of the reaction product was removed, and the residual product was dried in vacuo by using a rotary evaporator at a temperature of 50° C. To the obtained product, a solution prepared by dissolving 0.02 g of Congo Red into 100 ml of water was added. The resultant mixture was completely dried again in vacuo by using a rotary evaporator to prepare a detecting agent.

(Measurement of the detecting ability 2)

Two glass tubes which were the same as those used in Example 1 were packed each with 2.0 g of the detecting agent prepared above. Nitrogen gas containing 10 ppm of chlorine or 50 ppm of hydrogen chloride was passed through the glass tubes packed with the detecting agent at the superficial velocity in a column of 5.9 cm/sec to bring the detecting agent into contact with the gas, and the time passed before the discoloration started was measured.

The results are shown in Table 2.

TABLE 2

| | gas to be detected | | time before start |
|---|---|---|---|
| | type | concentration (ppm) | of discoloration (min) |
| Example 10 | chlorine | 10 | <1 |
| Example 11 | hydrogen chloride | 50 | <1 |

EXAMPLES 12 AND 13

(Preparation of a detecting agent 3)

The same granular silica gel as that used in Example 1 in an amount of 100 g was impregnated with a solution prepared by dissolving 20.0 g of manganese sulfate tetra- and pentahydrates into 153 ml of water. After 250 ml of a 1N aqueous solution of sodium hydroxide was added to the impregnated product, the components were mixed together. The resultant mixture was left standing with intermittent stirring for 12 hours to allow the reaction to proceed. The supernatant fluid of the reaction product was removed, and the residual product was dried in vacuo by using a rotary evaporator at a temperature of 50° C. To the obtained product, a solution prepared by dissolving 0.02 g of Congo Red into 100 ml of water was added, and the components were mixed together. The resultant mixture was completely dried again in vacuo by using a rotary evaporator to prepare a detecting agent.

(Measurement of the detecting ability 3)

Two glass tubes which were the same as those used in Example 1 were packed each with 2.0 g of the detecting agent prepared above. Nitrogen gas containing 10 ppm of chlorine or 50 ppm of hydrogen chloride was passed through the glass tubes packed with the detecting agent at the superficial velocity in a column of 5.9 cm/sec to bring the detecting agent into contact with the gas, and the time passed before the discoloration started was measured.

The results are shown in Table 3.

TABLE 3

| | gas to be detected | | time before start of discoloration (min) |
|---|---|---|---|
| | type | concentration (ppm) | |
| Example 12 | chlorine | 10 | <1 |
| Example 13 | hydrogen chloride | 50 | <1 |

EXAMPLES 14 AND 15

(Preparation of a detecting agent 4)

Activated alumina having a grain size of 8 to 16 mesh, a specific surface area of 210 m²/g, a pore volume of 0.99 ml/g, and a bulk density of 0.68 g/ml (a product of MIZUSAWA KAGAKU KOGYO Co., Ltd.; NEOBEADS GB8~16) in an amount of 150 g was impregnated with a solution prepared by dissolving 5.0 g of cobalt nitrate hexahydrate into 153 ml of water. After 50 ml of a 1N aqueous solution of sodium hydroxide was added to the impregnated product, the components were mixed together. The resultant mixture was left standing with intermittent stirring for 12 hours to allow the reaction to proceed. The supernatant fluid of the reaction product was removed, and the residual product was dried in vacuo by using a rotary evaporator at a temperature of 50° C. To the obtained product, a solution prepared by dissolving 0.1 g of Congo Red into 100 ml of water was added, and the components were mixed together. The resultant mixture was completely dried again in vacuo by using a rotary evaporator to prepare a detecting agent.

(Measurement of the detecting ability 4)

Two glass tubes which were the same as those used in Example 1 were packed each with 2.0 g of the detecting agent prepared above. Nitrogen gas containing 10 ppm of chlorine or 50 ppm of hydrogen chloride was passed through the glass tubes packed with the detecting agent at the superficial velocity in a column of 5.9 cm/sec to bring the detecting agent into contact with the gas, and the time passed before the discoloration started was measured.

The results are shown in Table 4.

TABLE 4

| | gas to be detected | | time before start of discoloration (min) |
|---|---|---|---|
| | type | concentration (ppm) | |
| Example 14 | chlorine | 10 | 5 |
| Example 15 | hydrogen chloride | 50 | <1 |

EXAMPLES 16 AND 17

(Preparation of a detecting agent 5)

To 100 g of nickel hydroxide sesquihydrate, a solution prepared by dissolving 0.04 g of Congo Red into 22 g of water was added, and then 2 ml of a 1N aqueous solution of sodium hydroxide was added to the obtained mixture. The obtained paste was placed into a mold and dried at 50° C. under an atmosphere of nitrogen. The obtained product was pulverized into granules of 6 to 10 mesh to prepare a detecting agent.

(Measurement of the detecting ability 5)

Two glass tubes which were the same as those used in Example 1 were packed each with 2.0 g of the detecting agent prepared above. Nitrogen gas containing 10 ppm of chlorine or 50 ppm of hydrogen chloride was passed through the glass tubes packed with the detecting agent at the superficial velocity in a column of 5.9 cm/sec to bring the detecting agent into contact with the gas, and the time passed before the discoloration started was measured.

The results are shown in Table 5.

TABLE 5

| | gas to be detected | | time before start of discoloration (min) |
|---|---|---|---|
| | type | concentration (ppm) | |
| Example 16 | chlorine | 10 | 9 |
| Example 17 | hydrogen chloride | 50 | <1 |

EXAMPLE 18

(Confirmation of the absence of the effect of nitrogen gas)

A glass tube having an inner diameter of 19 mm was packed with 2.0 g of the detecting agent prepared in Example 1. Nitrogen gas consisting of 100% nitrogen was passed through the prepared glass tube packed with the detecting agent at the superficial velocity in a column of 6.4 cm/sec to bring the detecting agent into contact with the gas, and the change in color was observed. No change in color was found after 7200 minutes.

EXAMPLES 19 AND 20

(Measurement of the detecting ability 6)

Two glass tubes which were the same as those used in Example 1 were packed each with 2.0 g of the same detecting agent as that used in Example 18. Nitrogen gas containing 10 ppm of chlorine or 50 ppm of hydrogen chloride was passed through the glass tubes packed with the detecting agent at the superficial velocity in a column of 5.9 cm/sec to bring the detecting agent into contact with the gas, and the time passed before the discoloration started was measured.

The results are shown in Table 6.

TABLE 6

| | gas to be detected | | time before start of discoloration (min) |
|---|---|---|---|
| | type | concentration (ppm) | |
| Example 19 | chlorine | 10 | <1 |
| Example 20 | hydrogen chloride | 50 | <1 |

EXAMPLES 21 TO 24

(Measurement of the detecting ability 7)

Four glass tubes having an inner diameter of 19 mm were packed each with 2.0 g of the same detecting agent as that used in Examples 1 to 9. Nitrogen gas containing hydrogen fluoride, silicon tetrafluoride, boron trifluoride, or silicon tetrachloride, each in an amount of 50 ppm, was passed through the glass tubes packed with the detecting agent at the superficial velocity in a column of 5.9 cm/sec to bring the detecting agent into contact with the gas, and the time passed before the discoloration started was measured.

The results are shown in Table 7.

TABLE 7

| | gas to be detected | | time before start of discoloration (min) |
|---|---|---|---|
| | type | concentration (ppm) | |
| Example 21 | hydrogen fluoride | 50 | <1 |
| Example 22 | silicon tetrafluoride | 50 | <1 |
| Example 23 | boron trifluoride | 50 | <1 |
| Example 24 | silicon tetrachloride | 50 | <1 |

EXAMPLE 25 AND 26

(Preparation of a detecting agent 6)

Activated alumina having a grain size of 8 to 16 mesh, a specific surface area of 210 m$^2$/g, a pore volume of 0.99 ml/g, and a bulk density of 0.68 g/ml (a product of MIZUSAWA KAGAKU KOGYO Co., Ltd.; NEOBEADS GB8~16) was used as the support in an amount of 150 g, and the support was impregnated with a solution prepared by dissolving 5.0 g of cobalt nitrate hexahydrate into 153 ml of water. After 50 ml of a 1N aqueous solution of sodium hydroxide was added to the impregnated product, the components were mixed together. The resultant mixture was left standing with intermittent stirring for 12 hours to allow the reaction to proceed. Then, the supernatant fluid was removed, and the residual product was dried in vacuo by using a rotary evaporator at a temperature of 50° C. to remove the residual water. To the obtained product, a solution prepared by dissolving 0.1 g of Congo Red into 100 ml of water was added, and the components were mixed together. The resultant mixture was completely dried again in vacuo by using a rotary evaporator to prepare a detecting agent.

(Measurement of the detecting ability 8)

Two glass tubes which were the same as those used in Example 1 were packed each with 2.0 g of the detecting agent prepared above. Nitrogen gas containing 10 ppm of chlorine or 50 ppm of hydrogen chloride was passed through the glass tubes packed with the detecting agent, and the time passed before the discoloration started was measured.

The results are shown in Table 8.

EXAMPLES 27 AND 28

(Preparation of a detecting agent 7)

A detecting agent was prepared in accordance with the same procedures as those conducted in Examples 25 and 26 except that 150 g of titania having a spherical shape of a diameter of 5 mm, a specific surface area of 39 m$^2$/g, and a pore volume of 0.33 ml/g (a product of NISSAN GARDLER Co., Ltd.; CS-300-46) was used as the support.

(Measurement of the detecting ability 9)

The detecting agent prepared above was brought into contact with nitrogen gas containing chlorine or hydrogen chloride in accordance with the same procedures as those conducted in Examples 25 and 26, and the time passed before the discoloration started was measured.

The results are shown in Table 8.

EXAMPLES 29 AND 30

(Preparation of a detecting agent 8)

A detecting agent was prepared in accordance with the same procedures as those conducted in Examples 25 and 26 except that 150 g of zirconia having a diameter of 2 to 3 mm, a length of about 5 mm, a specific surface area of 90 m$^2$/g, and a pore volume of 0.31 ml/g (a product of NORTON Company; XZ-16052) was used as the support.

(Measurement of the detecting ability 10)

The detecting agent prepared above was brought into contact with nitrogen gas containing chlorine or hydrogen chloride in accordance with the same procedures as those conducted in Examples 25 and 26, and the time passed before the discoloration started was measured.

The results are shown in Table 8.

EXAMPLES 31 AND 32

(Preparation of a detecting agent 8)

A detecting agent was prepared in accordance with the same procedures as those conducted in Examples 25 and 26 except that 150 g of silica-alumina having a spherical shape of a diameter of 5 mm and a specific surface area of 80 m$^2$/g (a product of NORTON Company; SA377) was used as the support.

(Measurement of the detecting ability 11)

The detecting agent prepared above was brought into contact with nitrogen gas containing chlorine or hydrogen chloride in accordance with the same procedures as those conducted in Examples 25 and 26, and the time passed before the discoloration started was measured.

The results are shown in Table 8.

TABLE 8

| | type of support | gas to be detected | | time before start of discoloration (min) |
|---|---|---|---|---|
| | | type | concentration (ppm) | |
| Example 25 | activated alumina | chlorine | 10 | 5 |
| Example 26 | activated alumina | hydrogen chloride | 50 | <1 |
| Example 27 | titania | chlorine | 10 | 5 |
| Example 28 | titania | hydrogen chloride | 50 | <1 |
| Example 29 | zirconia | chlorine | 10 | 6 |
| Example 30 | zirconia | hydrogen chloride | 50 | <1 |
| Example 31 | silica-alumina | chlorine | 10 | 5 |
| Example 32 | silica-alumina | hydrogen chloride | 50 | <1 |

COMPARATIVE EXAMPLE 1

(Preparation of a detecting agent 10)

To 100 g of granular silica gel having the same diameter as that of silica gel used in Example 1, a solution prepared by dissolving 0.1 g of Congo Red into 200 ml of water was added, and the residual water was removed from the resultant mixture by drying in vacuo using a rotary evaporator at a temperature of 50° C. to prepare a detecting agent.

(Measurement of the detecting ability 12)

A glass tube which was the same as that used in Example 1 was packed with 2.0 g of the detecting agent prepared above. Nitrogen gas containing 10 ppm of chlorine was passed through the glass tube packed with the detecting agent at the superficial velocity in a column of 5.9 cm/sec to bring the detecting agent into contact with the gas, and the time passed before the discoloration started was measured.

As the result, the detecting agent lost its color within one minute of passing the gas through the tube.

What is claimed is:

1. A detecting agent for detecting at least one member selected from the group consisting of halogen gases and acidic gases which is contained in a gas, wherein the detecting agent comprises a discoloring component which comprises a hydroxide of a transition metal and Congo Red.

2. A detecting agent according to claim 1, wherein the transition metal is at least one metal selected from the group consisting of nickel (II), cobalt (II), and manganese (II).

3. A detecting agent according to claim 1, wherein the ratio by weight of the hydroxide of a transition metal to Congo Red is in a range of 1:(0.01 to 0.00001).

4. A detecting agent according to claim 1, wherein the halogen gases are selected from the group consisting of fluorine gas, chlorine gas, bromine gas, chlorine fluoride gas, and chlorine trifluoride gas.

5. A detecting agent according to any of claim 1, wherein the acidic gases are selected from the group consisting of hydrogen fluoride, tungsten hexafluoride, silicon tetrafluoride, boron trifluoride, hydrogen chloride, silicon tetrachloride, and boron trichloride.

6. A detecting agent according to claim 1, wherein the hydroxide of a transition metal and Congo Red are supported on an inorganic support.

7. A detecting agent according to claim 6, wherein the hydroxide of a transition metal is cobalt (II) hydroxide and the inorganic support is silica gel.

8. A detecting agent according to claim 6, wherein the inorganic support is at least one member selected from the group consisting of silica gel, silica-alumina, titania, alumina, and zirconia.

9. A detecting agent according to claim 6, wherein the ratio by weight of the support to the hydroxide of a transition metal and Congo Red is in a range of 1:(0.15 to 0.0001):(0.1 to 0.00001).

10. A detecting agent according to claim 7, wherein the ratio by weight of the support to the hydroxide of a transition metal and Congo Red is in a range of 1:(0.15 to 0.0001):(0.1 to 0.00001).

11. A detecting agent according to claim 8, wherein the ratio by weight of the support to the hydroxide of a transition metal and Congo Red is in a range of 1:(0.15 to 0.0001):(0.1 to 0.00001).

12. A detecting agent according to claim 2, wherein the hydroxide of a transition metal and the Congo Red are supported on an inorganic support and the ratio by weight of the support to the hydroxide of a transition metal and Congo Red is in a range of 1:(0.15 to 0.0001):(0.1 to 0.00001).

13. A detecting agent according to claim 9, wherein the ratio by weight of the support to the hydroxide of the transition metal and to the Congo Red is 1:(0.05 to 0.005):(0.01 to 0.0001).

14. A detecting agent according to claim 10, wherein the ratio by weight of the support to the hydroxide of the transition metal and to the Congo Red is 1:(0.05 to 0.005):(0.01 to 0.0001).

15. A detecting agent according to claim 11, wherein the ratio by weight of the support to the hydroxide of the transition metal and to the Congo Red is 1:(0.05 to 0.005):(0.01 to 0.0001).

16. A detecting agent according to claim 12, wherein the ratio by weight of the support to the hydroxide of the transition metal and to the Congo Red is 1:(0.05 to 0.005):(0.01 to 0.0001).

* * * * *